(12) United States Patent
Shaw

(10) Patent No.: US 6,524,325 B2
(45) Date of Patent: Feb. 25, 2003

(54) HAEMOSTAT SHODS

(75) Inventor: David Shaw, Christchurch (NZ)

(73) Assignee: Ovation Medical Limited (NZ)

( * ) Notice: Subject to any disclaimer, the term of this patent is extended or adjusted under 35 U.S.C. 154(b) by 0 days.

(21) Appl. No.: 09/790,161

(22) Filed: Feb. 21, 2001

(65) Prior Publication Data

US 2001/0039433 A1 Nov. 8, 2001

(30) Foreign Application Priority Data

Feb. 22, 2000 (NZ) ................................................. 502998

(51) Int. Cl.⁷ ................................................ A61B 17/28
(52) U.S. Cl. ...................................................... 606/207
(58) Field of Search .................. 606/207, 148, 606/210, 211

(56) References Cited

U.S. PATENT DOCUMENTS

| | | | | | |
|---|---|---|---|---|---|
| 2,404,224 A | * | 7/1946 | Fink | ................................ | 294/28 |
| 4,005,893 A | * | 2/1977 | Tash | ................................ | 294/28 |
| 4,457,756 A | * | 7/1984 | Kern et al. | ................. | 604/286 |
| 4,583,671 A | * | 4/1986 | Cressy | ........................ | 227/144 |
| 4,834,090 A | * | 5/1989 | Moore | ........................ | 128/303 |
| 5,250,072 A | * | 10/1993 | Jain | ........................... | 606/205 |
| 5,609,599 A | * | 3/1997 | Levin | .......................... | 606/153 |

* cited by examiner

Primary Examiner—John J. Calvert
Assistant Examiner—James G Smith
(74) Attorney, Agent, or Firm—McDermott, Will & Emery

(57) ABSTRACT

This invention relates to surgical instrument jaw covers, and particularly hemostat shods. The jaw covers include a pair of spaced-apart shods interconnected by a bridging member, each shod having an opening to a bore adapted to accommodate a tip of a jaw of a surgical instrument, and the bridging member defining a separation distance between the openings.

16 Claims, 3 Drawing Sheets

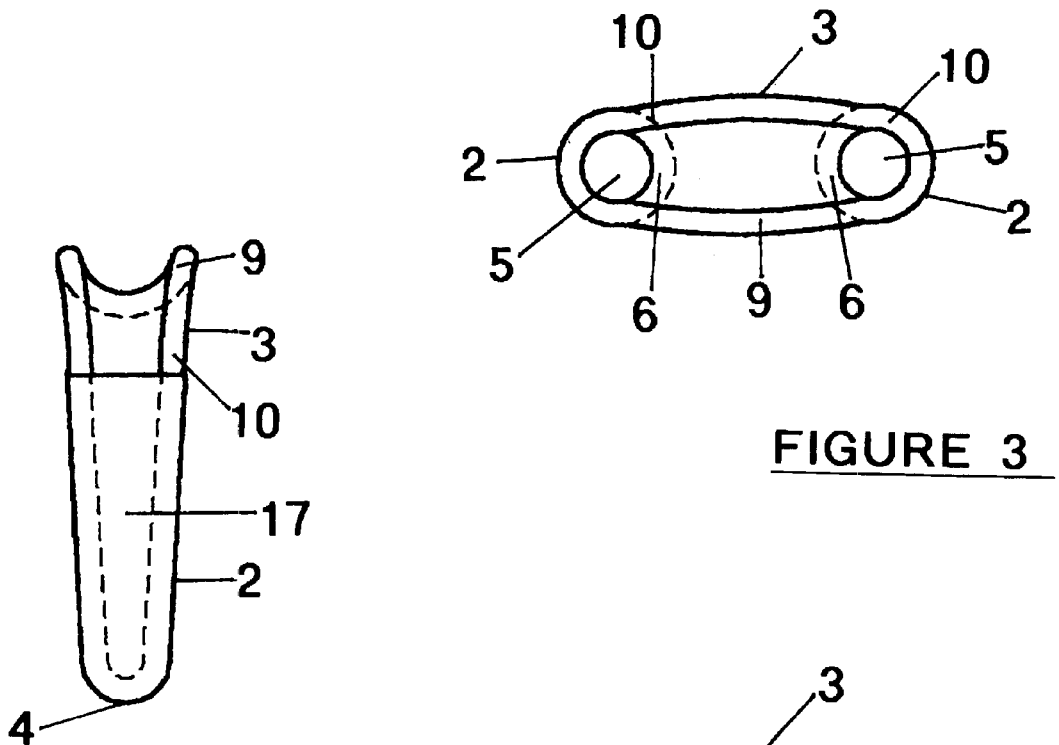
FIGURE 3
FIGURE 5
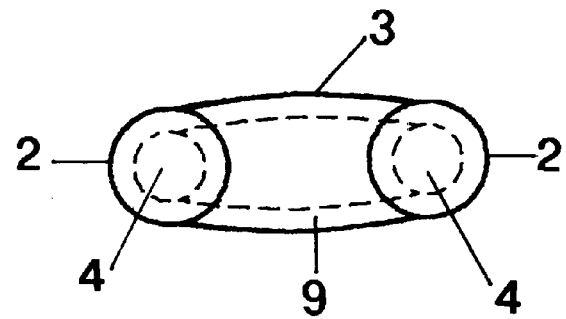
FIGURE 4

HAEMOSTAT SHODS

FIELD OF THE INVENTION

This invention relates to surgical instrument jaw covers, and in particular haemostat shods.

BACKGROUND OF THE INVENTION

Haemostats are used in surgery for gripping or clamping blood vessels and also for grasping sutures. The jaws of haemostats are serrated and these serrations can result in damage to sutures. To reduce the risk of damage small rubber or plastic covers have been developed for covering the tips of each jaw of a haemostat. Such covers are known as "shods" or suture boots.

Available shods are produced singly although generally sold in sets of pairs of separate shods. A pair of shods are used once only and then discarded.

To enable single shods to be used effectively they generally must be presented in a way providing for convenient engagement of a pair of separate shods over each jaw tip simultaneously. This can require bulky or complex packaging.

A further problem associated with the use of haemostats for tying sutures is the risk of the suture becoming engaged or entangled in the hinge of the haemostat.

A further problem arises from the fact that existing shods cover only a part of the haemostat "teeth". Thus, there is only a small area of the haemostat jaws that can be used to grip a suture, and a surgeon must be careful to line up the suture with the shod surface to avoid damaging the suture.

U.S. Pat. No. 4,834,090 discloses a form of disposable suture boot which comprises a sealed elongate monolithic unitary hollow cylindrical body of resilient surgical rubber. The cylindrical body is cut at a mid-point to form an interconnecting web between the sealed tube ends which form the suture boots. For these suture boots to work the material they are made from must be of sufficient resilience to allow the jaws of the surgical instrument to open. However, the interconnecting web still needs to stretch, and this will interfere with the ordinary operation of the instrument. There is also a potential problem of this web snapping whilst the device is being engaged on a surgical instrument or during operation of the instrument, with the added problem of sutures then becoming trapped on the surgical instrument. Further, the close proximity of the open ends of the tube, and the fact that the tube must be physically folded into a V-shape by the user before it can be engaged on the jaws, makes engagement on the jaw tips difficult.

In addition, with the suture boots being formed from a unitary hollow tube, ie, with parallel sides, there can be difficulties associated with fully engaging the boots onto generally tapered jaws of surgical instruments.

Thus, it is an object of the present invention to provide surgical instrument jaw covers which reduce or overcome at least some of the above mentioned problems, or which at least provides the public with a useful alternative. In particular, it is an object of the invention to provide instrument jaw covers which are easier and/or more convenient to engage on a surgical instrument, and/or which better protect sutures from damage by the instrument without interfering with effective operation of the instrument.

Other objects of the invention may become apparent from the following description which is given by way of example only.

SUMMARY OF THE INVENTION

According to one aspect of the present invention there is provided surgical instrument jaw covers including a pair of spaced-apart shods interconnected by a bridging member, each shod having an opening to a bore adapted to accommodate a tip of a jaw of a surgical instrument and the bridging member defining a separation distance between the openings.

Preferably, the bridging member may be integrally formed with the shods.

Preferably, a mid-portion of the bridging member, between the openings of the shods, may be wider than portions adjacent the shods.

Preferably, the separation distance may be in the range 5–15 mm.

Preferably, the separation distance may be substantially 10 mm.

Preferably, each bore may be tapered, wider at the opening than at the opposite, closed, longitudinal end.

Other aspects of the present invention may become apparent from the following description which is given by way of example and with reference to the accompanying drawings in which:

BRIEF DESCRIPTION OF THE DRAWINGS

FIG. 3: Shows a top end view (from A) of the covers of FIG. 1;

FIG. 4: Shows a bottom end view (from B) of the covers of FIG. 1;

FIG. 5: Shows an end view of the covers of FIG. 1;

DETAILED DESCRIPTION OF THE PRESENTLY PREFERRED EMBODIMENTS

Figure 1:
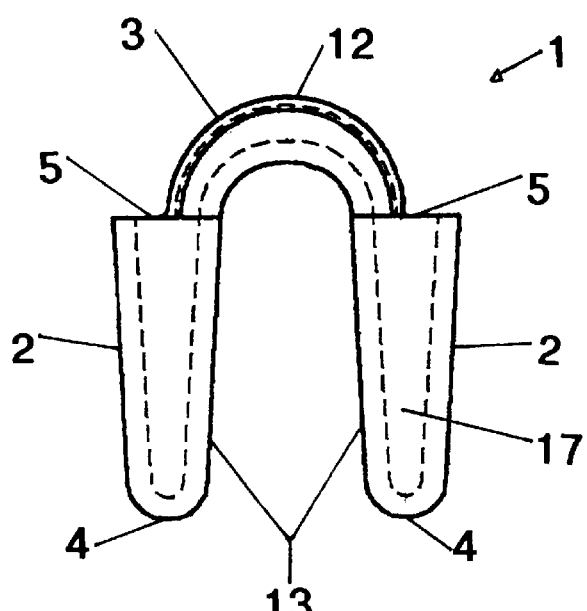
FIG. 1: Shows a side view of surgical instrument jaw covers of the invention in one preferred form.
Figure 2:
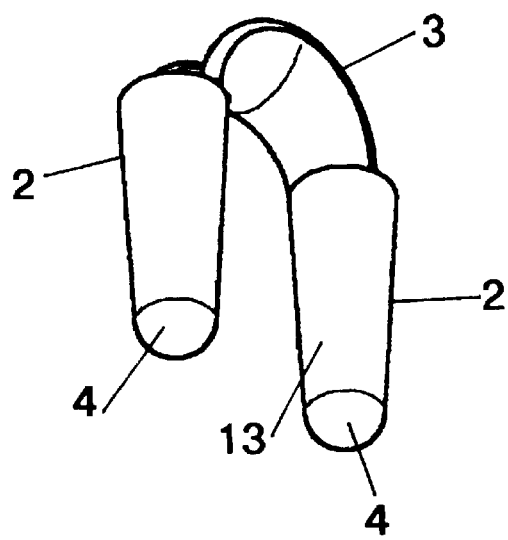
FIG. 2: Shows an isometric view of the jaw covers of FIG. 1.

With reference to the figures, the surgical instrument jaw covers 1 of the invention include a pair of shods 2 interconnected by a bridging member 3. Each shod 2 is closed at one end 4 and has an opening 5 at the opposite end to a central bore. In use the tip of a surgical instrument jaw is engagable into the bore of a shod.

The bridging member 3 interconnects the shods 2 adjacent one side 6 of each opening 5.

With reference to FIGS. 3–5, a mid portion 9 of the bridging member 3 is wider than the end portions 10. This wider portion 9 helps, in use, to isolate a suture gripped between the shods from the hinge of the instrument.

In the embodiment of FIG. 1 the shods 2 are substantially parallel to one another with their openings 5 pointing in the same direction. The bridge member 3 curves away from the shods. It could alternatively be angled in this direction with a "fold" at the apex 12. Such a configuration ensures that the bridging member 3, in use, does not intrude on the working space between engagement surfaces 13 of the shods 2 when gripping a suture.

Figure 6:
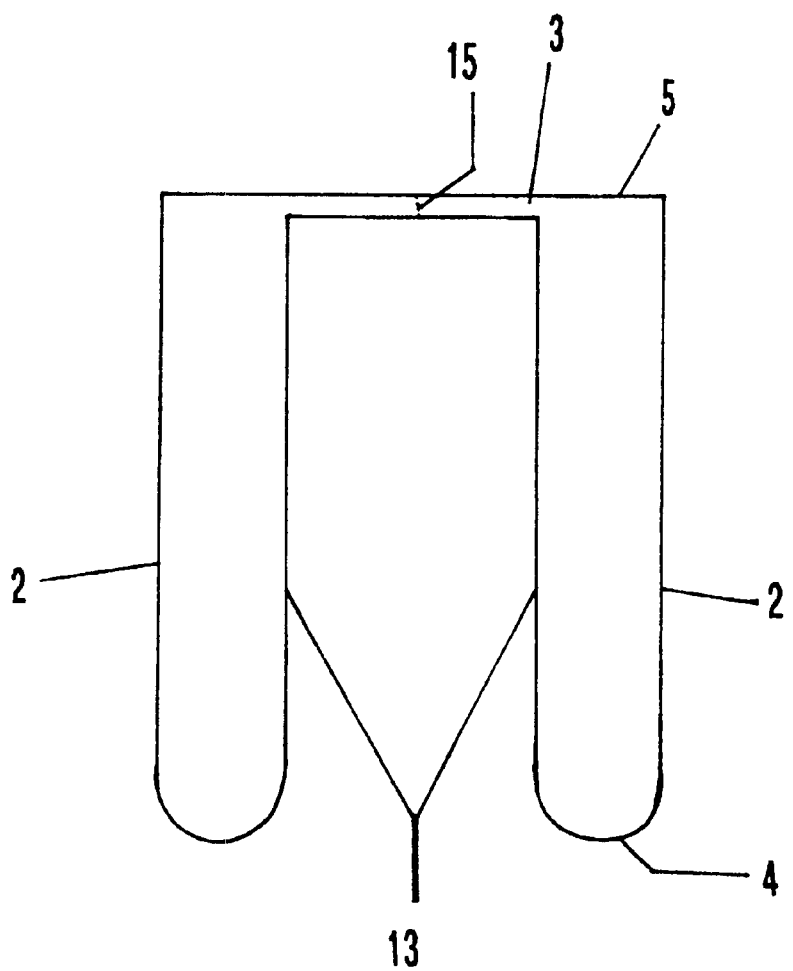
FIG. 6: Shows a side view of covers of the invention in an alternative embodiment.

In the embodiment to FIG. 6, the bridging member 3 is substantially perpendicular to the shods 2. With such an embodiment there is preferably a fold or hinge point at a mid point 15 on the bridging member 3 between the shods 2 adapted to facilitate hinging or flexing of the bridging member towards the instrument hinge, and therefore away from the space between the engagement surfaces 13 of the shods 2, in use.

The bridging member 3 is of a sufficient length, or configured in such a way as to fix a resting distance between the centres of the openings 5 of the shods 2 between about 5 mm and 15 mm. In a preferred form the centre:centre distance is about 10 mm, to facilitate engagement of the shods onto both jaw tips simultaneously.

Outer surfaces 16 and the bore of 17 of the shods themselves are tapered, with the closed ends 4 being narrower than ends having the openings 5. Alternatively the outer surfaces of the shods could be parallel (as in FIG. 6) and just the bores 17 tapered. The wider openings 5 facilitate engagement of the shods on the jaw tips, whilst the taper facilities engagement of the jaw ends to the closed ends 4 of the shods whilst ensuring secure engagement.

The surgical instrument jaw covers of the invention may be made from a medical-grade plastic, rubber or other synthetic material, for example, Santoprene. At least the bridging member is flexible. Preferably the shods and bridging member are integrally formed.

A radio-opaque material may be included in the manufacturing material so that if shods are inadvertently left in a patient after an operation they will be visible on x-ray. The jaw covers will also preferably be a bright colour, optionally luminescent, to ensure that they are clearly visible and contrast well with the colour of blood.

Thus, the jaw covers of the invention can be simply, quickly and securely engaged on the adjacent tips of surgical instrument jaws. They protect against sutures from becoming trapped in the hinge of the instrument, and a surgeon using an instrument with such jaw covers does not have to be concerned about the precise placing of a suture within the jaws since the bridging member prevents the suture from being engaged between uncovered portions of the metal jaws.

Wherein the foregoing description reference has been made to specific components or integers of the invention having known equivalents then such equivalents are herein incorporated as if individually set forth.

Although this invention has been described by way of example and with reference to possible embodiments thereof it is to be understood that modifications or improvements may be made thereto without departing from the scope or spirit of the invention.

What is claimed is:

1. Surgical instrument jaw covers comprising a pair of spaced-apart shods interconnected by a bridging member, each shod having an opening to a bore adapted to accommodate a tip of a jaw of a surgical instrument and the bridging member defining a separation distance in the range of about 5 mm to about 15 mm between the openings.

2. The surgical instrument jaw covers according to claim 1 wherein the separation distance is about 10 mm.

3. The surgical instrument jaw covers according to claim 1 wherein the bridging member is integrally formed with the shods.

4. The surgical instrument jaw covers according to claim 1 wherein a mid-portion of the bridging member, between the openings of the shods, is wider than portions of the bridging member adjacent the shods.

5. The surgical instrument jaw covers according to claim 1 wherein the bore of each shod is tapered, being wider at the opening than at an opposite, closed, longitudinal end.

6. The surgical instrument jaw covers according to claim 1 wherein the shods themselves are tapered.

7. The surgical instrument jaw covers according to claim 1 wherein the shods are substantially parallel to one another with their openings pointing in the same direction.

8. The surgical instrument jaw covers according to claim 1 wherein the bridging member is adapted not to interfere with a working space between adjacent surfaces of the shods which, in use, grip an item between the jaws of the surgical instrument.

9. Surgical instrument jaw covers comprising a pair of spaced-apart shods interconnected by a bridging member, each shod having an opening to a bore adapted to accommodate a tip of a jaw of a surgical instrument and the bridging member defining a separation distance of about 10 mm between the openings.

10. The surgical instrument jaw covers according to claim 9 wherein the bridging member is integrally formed with the shods.

11. Surgical instrument jaw covers comprising a pair of spaced-apart shods interconnected by a bridging member, each shod having an opening to a bore adapted to accommodate a tip of a jaw of a surgical instrument and the bridging member defining a separation distance between the openings such that the bridging member forms a mid-portion between the openings of the shods that is wider than portions of the bridging member adjacent the shods.

12. The surgical instrument jaw covers according to claim 11 wherein the bridging member is adapted not to interfere with a working space between adjacent surfaces of the shods which, in use, grip an item between the jaws of the surgical instrument.

13. Surgical instrument jaw covers comprising a pair of spaced-apart shods interconnected by a bridging member, each shod having an opening to a bore, wherein said bore is wider at the opening than at an opposite, closed longitudinal end, and further wherein each shod is tapered so that it is adapted to accommodate a tip of a jaw of a surgical instrument, and the bridging member defining a separation distance between the openings.

14. Surgical instrument jaw covers comprising a pair of spaced-apart shods interconnected by a bridging member, each shod having an opening to a bore, wherein said bore is wider at the opening than at an opposite, closed longitudinal end, and further wherein each bore is tapered so that it is adapted to accommodate a tip of a jaw of a surgical instrument, and the bridging member defining a separation distance between the openings.

15. A kit comprising:

(a) surgical instrument jaw covers comprising a pair of spaced-apart shods interconnected by a bridging member, each shod having an opening to a bore adapted to accommodate a tip of a jaw of a surgical instrument and the bridging member defining a separation distance in the range of about 5 mm to about 15 mm between the openings; and (b) a surgical instrument including jaws capable of insertion within said surgical instrument jaw covers.

16. A kit comprising:

(a) surgical instrument jaw covers comprising a pair of spaced-apart shods interconnected by a bridging member, each shod having an opening to a bore adapted to accommodate a tip of a jaw of a surgical instrument and the bridging member defining a separation distance between the openings such that the bridging member forms a mid-portion between the openings of the shods that is wider than portions of the bridging member adjacent the shods; and (b) a surgical instrument including jaws capable of insertion within said surgical instrument jaw covers.

* * * * *